United States Patent [19]

Stapp et al.

[11] Patent Number: 5,101,029
[45] Date of Patent: Mar. 31, 1992

[54] ISOCYANURATE-CONTAINING ORGANOSILICON COMPOUNDS

[75] Inventors: Bernhard Stapp, Kalchreuth; Helmut Markert, Nuremberg; Lothar Schoen, Neunkirchen, all of Fed. Rep. of Germany

[73] Assignee: Siemens Aktiengesellschaft, Berlin & Munich, Fed. Rep. of Germany

[21] Appl. No.: 504,977

[22] Filed: Apr. 5, 1990

[30] Foreign Application Priority Data

Apr. 27, 1989 [DE] Fed. Rep. of Germany ........ 3913980

[51] Int. Cl.$^5$ .............................................. C07D 251/30
[52] U.S. Cl. .......................................................... 544/221
[58] Field of Search ........................................... 544/221

[56] References Cited

U.S. PATENT DOCUMENTS

| | | | |
|---|---|---|---|
| 3,821,218 | 6/1974 | Berger | 260/248 |
| 3,892,643 | 7/1975 | Tanaka et al. | 204/159.13 |
| 4,855,378 | 8/1989 | Pradl et al. | 528/26 |

*Primary Examiner*—Johann Richter
*Attorney, Agent, or Firm*—Kenyon & Kenyon

[57] ABSTRACT

The invention relates to isocyanurate-containing, organosilicon compounds of the general formula

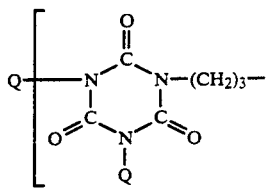

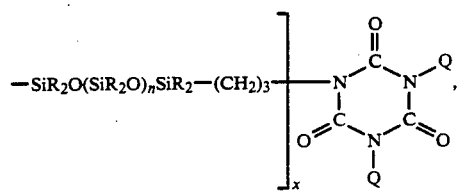

in which $Q = -(CH_2)_3SiR_2O(SiR_2O)_nSiR_2R'$, n is an integer from 0 to 25 and x is an integer from 0 to 10, and the following holds for the residues R and R', which can be the same or different:

R = alkyl, cycloalkyl, aryl, arylalkyl or alkylaryl, and
R' = an epoxy-functional residue with 4 to 10 C-atoms or a (meth)acrylate-functional residue with at least 6 C-atoms.

3 Claims, No Drawings

ISOCYANURATE-CONTAINING ORGANOSILICON COMPOUNDS

FIELD OF THE INVENTION

The invention relates to new isocyanurate-containing, organosilicon compounds as well as to a method for their preparation.

BACKGROUND OF THE INVENTION

Silicon-organic isocyanurates, such as 1,3,5-tris(-trialkoxysilylpropyl)-isocyanurate are known from the U.S. Pat. No. 382,218. These compounds, that can be used as adhesive agents, develop through the trimerization of the corresponding silylorganoisocyanates. The isocyanates, on the other hand, are prepared by effecting a reaction between silylorganohalides and metal cyanates, such as potassium cyanate.

Thermally hardenable compositions, consisting essentially of (a) a silicon-hydrogen compound with at least two hydrogen atoms bonded to the silicon atom and (b) at least one isocyanuric acid compound in the form of a trialkenylisocyanurate or of a derivative thereof, are known from the German Published Patent Application 24 21 038. These compositions can also contain an addition polymerization catalyst or this type of catalyst and a radical polymerization catalyst. The components (a) and (b) are usually mixed and hardened in an essentially equimolar ratio. During the hardening, products are formed that have good thermal resistance, mechanical strength and adhesive property.

A method for preparing organopolysiloxane elastomers is known from the German Published Patent Application 36 31 125, Wherein substances that are cross-linkable as a result of the attachment of Si-bonded hydrogen to SiC-bonded vinyl groups are cross-linked. The substances contain an additive to improve the adherence of the elastomers to the bases, on which they are produced. This additive can be, inter alia, an organosilicon compound that is obtained through the hydrosilylation of triallylisocyanurate with an organosiloxane of the formula $HSi(CH_3)_2[OSi(CH_3)_2]_nH$, in which n is a whole number with a value of 1 to 5. Isocyanurate-containing organosilicon compounds are thereby formed, whereby each isocyanurate nitrogen is bonded via a $(CH_2)_3$ grouping to a Si-H-functional polysiloxane chain, in particular—$Si(CH_3)_2OSi(CH_3)_2H$.

SUMMARY OF THE INVENTION

The invention provides isocyanurate-containing organosilicon compounds of the general formula

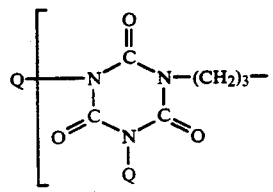

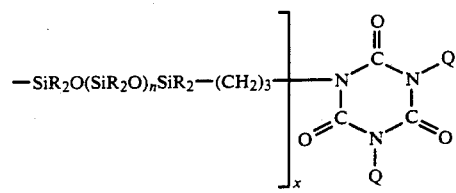

in which $Q=-(CH_2)_3SiR_2O(SiR_2O)_nSIR_2R'$, n is an integer from 0 to 25 and x is an integer from 0 to 10, and the following holds for the residues R and R', which can be the same or different:

R = alkyl, cycloalkyl, aryl, arylalkyl or alkylaryl, and
R' = an epoxy-functional residue with 4 to 10 C-atoms or a (meth)acrylate-functional residue with at least 6 C-atoms.

DETAILED DESCRIPTION OF THE INVENTION

The residues R in the above-defined compounds represent alkyl, cycloalkyl, aryl, arylalkyl or alkylaryl groups, where these groups can be unsubstituted or substituted. As an example, the following groups are named for the residues R:

alkyl with 1 to 4 C-atoms, such as methyl, ethyl, propyl, isopropyl, butyl and isobutyl, where the methyl residue is preferred;

cycloalkyl with 5 to 8 C-atoms, such as cyclohexyl, methylcyclohexyl and cycloheptyl;

aryl with 6 to 10 C-atoms, such as phenyl and naphthyl;

arylalkyl, such as β-phenylethyl, β-phenylpropyl, o-methylphenylethyl, 3.5-dimethylphenylethyl, p-nonylphenylethyl, o-bromophenylethyl, 3.5-dibromophenylethyl, p-chlorophenylethyl and 3.5-dichlorophenylethyl;

alkylaryl, such as tolyl.

The epoxy-functional residues R' have 4 to 10 C-atoms, where the epoxide group is bonded to the siloxane chain via a carbon bridge that can also contain heteroatoms. The residues R' are derived from vinyl- or allyl-functional epoxides in a manner such that the vinyl or allyl function is added to a Si-H function. For example, the following compounds are named as vinyl- or allyl-functional epoxides: allylglycidylether, 4-vinylcyclohexene oxide, 4-vinylnorbornene oxide and 1,2-epoxy-3-butene.

In the case of the (meth)acrylate-functional residues R' the (methy)acrylate group is likewise bonded to the siloxane chain via a carbon bridge. These residues can be derived from the epoxy-functional residues, and to be specific in a way such that a fission of the epoxide ring takes place by means of (meth)acrylic acid. In this case the (meth)acrylate-functional residues have 7 to 14 C-atoms. The (meth)acrylate group of the (meth)acrylate-functional residues R' can also be bonded ester-like or via a carbonate grouping or a urethane grouping to a carbon bridge leading to the siloxane chain.

Organosilicon compounds of the following type are preferred:

Compounds in the case of which the residues R' are epoxy-functional residues, which are derived from the following unsaturated epoxides: 1,2-epoxy-3-butene, 1,2-epoxy-5-hexene, 1,2-epoxy-7-octene, allylglycidylether, 4-vinylcyclohexene oxide, 4- vinylnorbornene oxide, norbornadiene oxide, limonene oxide and dicyclopentadiene oxide;

Compounds in the case of which the residues R' are (meth)acrylate-functional residues, produced through the ring fission of the epoxide residue of compounds of the above-mentioned type with (meth)acrylic acid;

Compounds in the case of which the residues R' are (meth)acrylate-functional residues, which are bonded ester-like or via a carbonate grouping or a urethane grouping to a carbon bridge leading to the siloxane chain.

The compounds according to the invention are new polymerizable, isocyanurate-containing, organosilicon compounds that have epoxy and/or (meth)acrylate functions. Thus, with the invention, liquid prepolymers are produced, in whose chemical composition rigid structural elements and flexible structural elements are united These prepolymers have reactive groups which enable a polymerization (of the prepolymers) to take place.

The isocyanurate-containing organosilicon compounds according to the invention can be prepared in several ways. With one method, epoxy-functional or hydroxy-functional organosilicon compounds are prepared in a first process step and, to be precise, by reacting unsaturated epoxides (with 4 to 10 carbon atoms) or unsaturated alcohols (with 3 to 5 carbon atoms) with organosilicon compounds of the structure $HSiR_2O(SiR_2O)_nSiR_2H$, that is to say with compounds that have two terminal Si—H bonds. In this so-called hydrosilylation reaction, the molar ratio of the organosilicon compound to the epoxide or alcohol generally amounts to 1:1 to 1.2:1, so that the reaction product in the average has one Si—H function.

The above named compounds, in particular allylglycidylether, are used as unsaturated epoxides. The following compounds can be used as unsaturated alcohols: allylalcohol, 2-methyl-2-propene-1-ol, 3-methyl-3-butene-1-ol, 1-butene-3-ol, 2-methyl-3-butene-2-ol and 3-methyl-2-butene-1-ol, where allylalcohol is preferred. The hydrosilylation of the unsaturated epoxides and alcohols takes place in a manner that is known per se (c.f.: U.S. Pat. No. 834,326, U.S. Pat. No. 4,293,678 and German Published Patent Application 33 16 166 as well as "J. Amer. Chem. Soc.", vol. 81 (1959), pp 2632 fol, or European Published Patent Application 0 159 729, U.S. Pat. No. 2,970,150 and German Published Patent Application 32 22 839). The starting components are thereby reacted with each other, generally at an elevated temperature, in the presence of a catalyst; suitable catalysts are metals of the eighth subgroup of the periodic table or corresponding metal compounds. A hydrosilylation reaction proceeds, for example, at approx. 100° C. in toluene as a solvent with hexachloroplatinum acid ($H_2PtCl_6.6 H_2O$) as a catalyst.

The epoxy-functional or hydroxy-functional organosilicon compounds of the above mentioned type are then reacted in a second process step with triallyl-1,3,5-triazine-2,4,6-trione (triallylisocyanurate). The reaction, that is the hydrosilylation, is thereby effected in such a way that at least equimolar quantities of Si-H functions are apportioned to the allyl functions.

The hydrosilylation itself takes place in an inert solvent, such as dioxan, tetrahydrofuran or toluene, preferably at atmospheric pressure and at temperatures of 80° to 120° C., in the presence of a noble metal catalyst. Possible catalysts are aluminum oxide coated with platinum, hexachloroplatinum acid or a platinum/vinylsiloxane complex. The quantity of the catalyst that is used depends on the type of catalyst and on the reaction temperature.

While the epoxy-functional, isocyanurate-containing, organosilicon compounds (1a) prepared in the second process step already represent compounds according to the invention, the corresponding hydroxy-functional isocyanurate-containing silicon compounds (2a) must still be converted into compounds according to the invention. This is achieved in that the hydroxy-functional compounds are reacted with a monofunctional (meth)acrylic acid derivative and, to be specific, in such a manner that the hydroxyl groups are at least partially converted (Meth)acrylate-functional isocyanurate-containing organosilicon compounds (3a) result thereby, in the case of which the (meth)acrylate functions can be partially replaced by hydroxyl functions. In a corresponding manner, the hydroxy-functional compounds can be converted with epichlorohydrin into epoxy-functional, isocyanurate-containing, organosilicon compounds (4a), whereby the epoxide functions likewise can be partially replaced by hydroxyl functions.

The epoxy-functional, isocyanurate-containing, organosilicon compounds (1a) also can be converted into (meth)acrylate-functional, isocyanurate-containing, organosilicon compounds (5a). To this end, the epoxy-functional compounds are reacted with (meth)acrylic acid in a manner such that the epoxide functions are completely or partially converted into (meth)acrylate functions. Therefore, with reference to 1 mole of epoxide, the quantity of (meth)acrylic acid can amount to between 0.5 and 5 mole.

In the above mentioned conversion, a fission of the epoxide ring takes place by means of the carboxylic acid, whereby a secondary hydroxyl group is formed (c.f.: U.S. Pat. No. 4,293,678 and U.S. Pat. No. 4,558,082). The reaction is carried out in inert solvents, such as toluene, at temperatures of between 25° and 120° C. (at atmospheric pressure), preferably at about 100° C., in the presence of an alkaline catalyst, in particular in the presence of an aminic catalyst. Suitable catalysts are, for example, benzyltrimethylammoniumchloride, benzyldimethylamine, dimethylaniline or 1,4-diazabicyclo[2,2,2]octan, that are applied in a quantity of 0.1 to 2% by weight, with reference to the epoxy-functional compound.

In the case of another method for preparing the isocyanurate-containing organosilicon compounds according to the invention, in a first process step, triallyl-1,3,5-triazine-2,4,6-trione is reacted with an organosilicon compound of the structure $HSiR_2O(SiR_2O)_nSiR_2H$ in the molar ratio of 1.1:1 to 2:1 to form an allyl-functional, isocyanurate-containing, organosilicon compound. The reaction takes place in a manner known per se in a solution and in the presence of a noble metal catalyst of the above mentioned type (c.f.: German Published Patent Application 24 21 038).

In this connection, reference is also made to the fact that it is possible to modify the organosiloxane constituent of the allyl-functional compounds. For that purpose, the allyl-functional compounds are equilibrated in the usual - acidic or alkaline -manner with other organosiloxanes, for example with octamethylcyclotetrasiloxane.

The allyl-functional, isocyanurate-containing, organosilicon compounds of the above mentioned type are reacted in a second process step with an epoxy-functional or a hydroxy-functional organosilicon compound, which—in the described manner—is obtained from an unsaturated epoxide (with 4 to 10 carbon atoms) or with an unsaturated alcohol (with 3 to 5 carbon atoms) and an organosilicon compound of the structure $HSiR_2O(SiR_2O)_nSiR_2H$. The reaction is effected thereby in the specified manner, whereby the quantities of the starting components are selected such that at least equimolar quantities of Si-H functions are apportioned to the allyl functions.

While the epoxy-functional, isocyanurate-containing, organosilicon compounds (1b) prepared in the second process step, again, already represent compounds according to the invention, the corresponding hydroxy-functional, isocyanurate-containing, organosilicon compounds (2b) must still be converted into compounds according to the invention. This is achieved—in the specified manner—through a reaction with a monofunctional (meth)acrylic acid derivative or with epichlorohydrin, whereby the hydroxyl groups are at least partially converted, so that (meth)acrylate-functional, isocyanurate-containing, organosilicon compounds (3b) or corresponding epoxy-functional compounds (4b) result, in the case of which the functional groups can be partially replaced by hydroxyl functions.

The following compounds can be used as monofunctional (meth)acrylic acid derivatives:

(meth)acrylic acid chloride:
  The reaction is effected by adding an aminic acid catching agent and by separating the amine hydrochloride that is produced; the (meth)acrylate functions are bonded, ester-like, in the final products.

(meth)acrylic acid ester:
  For example, methyl(meth)acrylate, ethyl(meth)acrylate, n-propyl(meth)acrylate and n-butyl(meth)acrylate are mentioned.

The reaction is effected, while the alcohol produced during the transesterification is removed by means of distillation; the (meth)acrylate functions are bonded, esterlike, in the final products.

Chloroformic acid esters of hydroxyfunctional (meth)acrylates:
  These are compounds of the general formula $$Cl-\underset{\underset{O}{\|}}{C}-O-\overset{*}{R}-O-\underset{\underset{O}{\|}}{C}-\underset{H(CH_3)}{C}=CH_2.$$

Multiple (meth)acrylic acid esters of pentaerythritol, trimethylolethane, trimethylolpropane and glycerol as well as their dimers, can thereby also be used as hydroxy-functional (meth)acrylates, that is as unsaturated alcohols. The reaction is effected by adding an aminic acid catching agent, and by separating the amine hydrochloride that is produced; the (meth)acrylate functions are bonded via carbonate groupings in the final products.

Isocyanate-functional (meth)acrylates:
  These are compounds of the general formula $$OCN-\overset{*}{R}-O-\underset{\underset{O}{\|}}{C}-\underset{H(CH_3)}{C}=CH_2.$$

Preferably, adducts of hydroxy-functional (meth)acrylates on diisocyanates are thereby applied, whereby the adducts in the average respectively have one isocyanate and one, (meth)acrylate function.

Preferably, 2,4-toluene diisocyanate and isophorone diisocyanate are used as the diisocyanate; suited hydroxy-functional (meth)acrylates are hydroxyethyl-, hydroxypropyl- and hydroxybutyl-(meth)acrylate, as well as caprolactone acrylate, trimethylolpropane-di(meth)acrylate, glycerol-di(meth)acrylate and pentaerythritoltri(meth)acrylate. The (meth)acrylate functions are bonded in the final products by way of urethane groupings.

The above described epoxy-functional isocyanurate-containing organosilicon compounds (1b) can also be converted into (meth)acrylate-functional, isocyanurate-containing, organosilicon compounds (5b). This takes place—as described previously—by effecting a reaction with (meth)acrylic acid. The epoxide functions, again, can thereby be completely or partially converted into (meth)acrylate functions.

The invention shall be explained in greater detail based on the following exemplified embodiments.

EXAMPLE 1

Preparation of an organosilicon compound of the structure $$H-\underset{\underset{CH_3}{|}}{\overset{\overset{CH_3}{|}}{Si}}-O-\underset{\underset{CH_3}{|}}{\overset{\overset{CH_3}{|}}{Si}}-(CH_2)_3-O-CH_2-\underset{\diagdown\phantom{O}\diagup}{CH}\underset{O}{\phantom{-}}CH_2$$

67.1 g of 1,1,3,3-tetramethyldisiloxane (0.5 mole), 300 ml toluene and 5 ml of a 0.01.molar solution of hexachloroplatinum acid in tetrahydrofuran are placed in a 1000 ml round-bottom flask provided with a reflux condenser, agitator, internal thermometer and dropping funnel. One adds to this by drops, a mixture of 57 g allylglycidylether (0.5 mole) and 50 ml toluene, while mixing within 10 hours at 95° C. After refluxing for 14 hours, the toluene and volatile components are removed at 50° C. and at a pressure of 15 mbar. A subsequent distillation yields 66 g of the desired product with the following data:

Boiling point: 73° C./0.1 mbar;
Refractive index $n_D^{20}$: 1.492;
SiH content: 0.402 mole/100 g;
Epoxide value 0.395 mole/100 g.

EXAMPLE 2

Preparation of an organosilicon compound of the structure $$H-\underset{\underset{CH_3}{|}}{\overset{\overset{CH_3}{|}}{Si}}-O-\underset{\underset{CH_3}{|}}{\overset{\overset{CH_3}{|}}{Si}}-(CH_2)_3-OH$$

67.1 of 1,1,3,3-tetramethyldisiloxane (0.5 mole), 100 ml toluene and—as a catalyst—2 g of an aluminum oxide coated with 1% platinum are placed in a 1000 ml round-bottom flask provided with a reflux condenser, agitator, internal thermometer and dropping funnel. One adds to this by drops, a mixture of 29 g allylalcohol (0.5 mole) and 100 ml toluene, while mixing within 4 hours at 60° C. After mixing for one hour at 60° C. and subsequently cooling to room temperature, the catalyst is separated off by means of pressure filtration through a membrane filter having a pore width of 0.45 μm. The toluene and volatile components are then removed at 50° C. and at a pressure of 15 mbar. A subsequent distillation yields 32.7 g of the desired product having the following data:
Boiling point: 50° to 54° C./0.2 mbar;
Refractive index $n_D^{20}$: 1.4190;
SiH content: 0.540 mole/100 g.

EXAMPLE 3

Preparation of an organosilicon compound of the structure

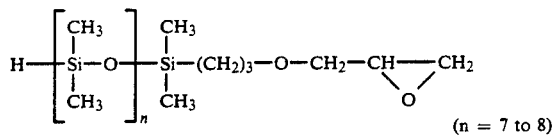
(n = 7 to 8)

129 g of a α, ω-SiH-functional polydimethylsiloxane (0.2 mole) with a SiH content of 0.31 mole/100 g, 500 ml toluene and 2 ml of a 0.02 molar solution of hexachloroplatinum acid in tetrahydrofuran are placed in a 1000 ml round-bottom flask provided with a reflux condenser, agitator, internal thermometer and dropping funnel. One adds to this by drops, a mixture of 22.8 g allylglycidylether (0.2 mole) and 100 ml toluene, while mixing, within 10 hours at 95° C. After refluxing for 14 hours, the toluene is removed at 50° C. and at a pressure of 15 mbar. Other volatile components are removed by heating for two hours to 70° C. at a pressure of 0.06 mbar. 123.5 g of the desired product are obtained having the following data:
Refractive index $n_D^{20}$: 1.4139;
SiH content: 0.129 mole/100 g;
Epoxide value: 0.114 mole/100 g.

EXAMPLE 4

Preparation of an organosilicon compound of the structure

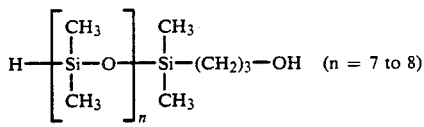
(n = 7 to 8)

In the manner as described in Example 2, 161.3 g of a α, ω-SiH-functional polydimethylsiloxane (0.25 mole) with a SiH content of 0.31 mole/100 g and 14.5 g allylalcohol (0.25 mole) are reacted. The toluene is then removed at 50° C. and at a pressure of 15 mbar. Other volatile components are removed by heating to 50° C. at a pressure of 0.06 mbar. 134 g of the desired product are obtained having the following data:
Refractive index $n_D^{20}$:1.4042;
SiH content: 0.142 mole/100 g.

EXAMPLE 5

Preparation of an epoxy-functional, isocyanurate-containing, organosilicon compound (1a) of the structure

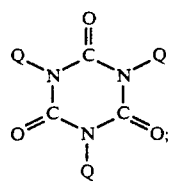

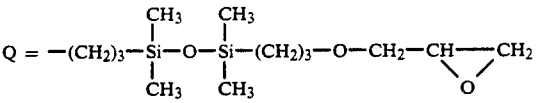

50 g of triallylisocyanurate (0.2 mole), 50 ml toluene and 6 ml of a 0.01 molar solution of hexachloroplatinum acid in tetrahydrofuran are placed in a 500 ml round-bottom flask provided with a reflux condenser, agitator, internal thermometer and dropping funnel. One adds to this by drops, a mixture of 149 g of the organosilicon compound (0.6 mole) prepared according to Example 1 and 100 ml toluene, while mixing, within 2 hours at 95° C. After refluxing for 4 hours, the toluene is removed at 50° C. and at a pressure of 15 mbar. Other volatile components are removed by heating to 100° C. at a pressure of 0.06 mbar. 183 g of the desired product are obtained as residue having the following data:
Viscosity at 25° C.: 220 mPa.s;
Refractive index $n_D^{20}$: 1.4710;
Epoxide value: 0.299 mole/100 g.

EXAMPLE 6

Preparation of an acrylate-functional, isocyanurate-containing, organosilicon compound (5a) of the structure

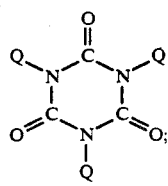

Q =

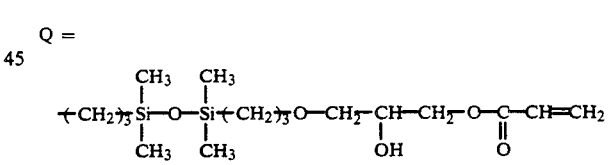

99.4 g of the epoxy-functional, isocyanurate-containing, organosilicon compound (0.1 mole) prepared according to Example 5, 100 ml toluene and 0.8 g N.N-dimethylbenzylamine are placed in a 500 ml round-bottom flask provided with a reflux condenser, agitator, internal thermometer and dropping funnel. One adds to this by drops, a mixture of 32.4 g of acrylic acid (0.45 mole) and 50 ml toluene, while mixing, at 100° C. within 30 minutes. The obtained solution is still heated for 19 hours to 100° C.; the toluene is then removed at 50° C. and at a pressure of 15 mbar. After adding 10 mg phenothiazine, solvent residues and unreacted acrylic acid are removed by heating to 70° C. at a pressure of 0.06 mbar. 97 g of the desired product are obtained as residue having the following data:
Viscosity at 25° C.: 2500 mPa.s;
Refractive index $n_D^{20}$: 1.4790;
Acrylate content: 0.252 mole/100 g.

EXAMPLE 7

Preparation of a hydroxy-functional, isocyanurate-containing, organosilicon compound (2a) of the structure

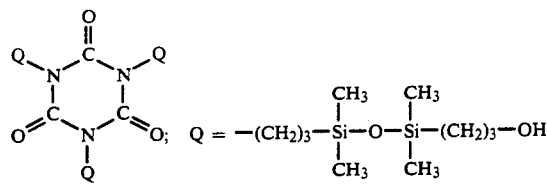

25 g of triallylisocyanurate (0.1 mole), 100 ml toluene and 0.3 ml of a platinum/divinyltetramethyldisiloxane complex (solution in xylene with 3 to 3.5% platinum, calculated as element) are placed in a 1000ml round-bottom flask provided with a reflux condenser, agitator, internal thermometer and dropping funnel. One adds to this by drops, a mixture of 57.7 g of the 1-(3-hydroxypropyl)-1,1,3,3-tetramethyldisiloxane (0.3 mol) prepared according to Example 2 and 250 ml toluene, while mixing, at 60° C. within 15 hours. This is then subsequently mixed for 2 hours at 60° C. After the toluene is removed at 50° C. and at a pressure of 15 mbar, 79.6 g of a viscous fluid, whose structure is confirmed through nuclear resonance and infrared absorption spectra, is obtained having the following data:
Viscosity at 25° C.: 1600 mPa.s;
Refractive index $n_D^{20}$: 1.4738.

EXAMPLE 8

Preparation of an acrylate-functional, isocyanurate-containing, organosilicon compound (3a) of the structure

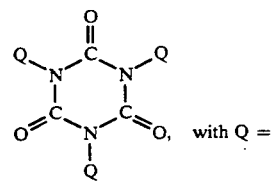, with Q =

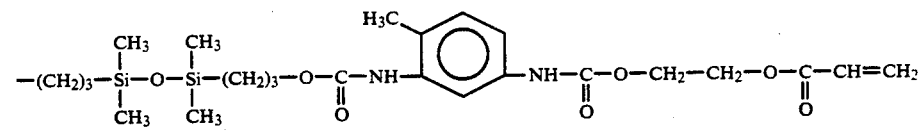

50 g of the hydroxy-functional, isocyanurate-containing, organosilicon compound (0.06 mole) prepared according to Example 7, 250 ml toluene, 0.01 g phenothiazine and 0.2 ml dibutyltindilaurate are placed in a 1000 ml round-bottom flask provided with an agitator, internal thermometer and dropping funnel. One adds to this by drops, a solution of 52.3 g of an isocyanate-functional acrylate (0.18 mole) in 250 ml toluene in such a manner that the temperature of the reaction mixture does not exceed 20° C. The isocyanate-functional acrylate was prepared by reacting 1 mole of 2,4-toluene diisocyanate with 1 mole of acrylic acid-2-hydroxyethylester (melting point: 42° C). After mixing for 20 hours at 20° C., solid components are separated off by means of pressure-filtration through a membrane filter having a pore width of 0.45 μm. After the toluene is removed at 50° C. and at a pressure of 15 mbar, 72 g of a highly viscous resin is obtained having the following data:
Viscosity at 25° C. 250000 mPa.s;
Refractive index $n_D^{20}$: 1.5198;
Acrylate content: 0.155 mole/100 g.

EXAMPLE 9

Preparation of an epoxy-functional, isocyanurate-containing, organosilicon compound (1b) of the structure

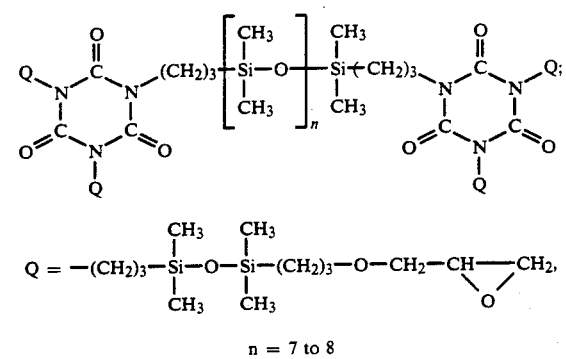

n = 7 to 8

50 g of triallylisocyanurate (0.2 mole), 100 ml toluene and 0.5 ml of a platinum/divinyltetramethyldisiloxane complex (solution in xylene with 3 to 3.5% platinum, calculated as element) are placed in a 1000 ml round-bottom flask provided with reflux condenser, agitator, internal thermometer and dropping funnel. One adds to this by drops, a mixture of 64.5 g of a α, ω-SiH-functional polydimethylsiloxane (0.1 mole) with a SiH content of 0.31 mole/100 g and 100 ml of toluene, while mixing, within 3 hours at 100° C. The reaction is completed after two hours at 100° C., as shown by the disappearance of the SiH band in the infrared spectrum at 2120 cm$^{-1}$. Subsequently, a mixture of 99.3 g of the organosilicon compound (0.4 mole) prepared according to Example 1 and 100 ml of toluene are added by drops, while mixing within two hours at 100° C. The reaction is completed after five hours at 100° C. The reprocessing is carried out as described in Example 5. 186 g of the desired product are obtained as residue having the following data:
Viscosity at 25° C.: 1000 mPa.s;
Refractive index $n_D^{20}$: 1.4602;
Epoxide value: 0.182 mole/100 g.

EXAMPLE 10

Preparation of an epoxy-functional, isocyanurate-containing, organosilicon compound (1b) of the structure

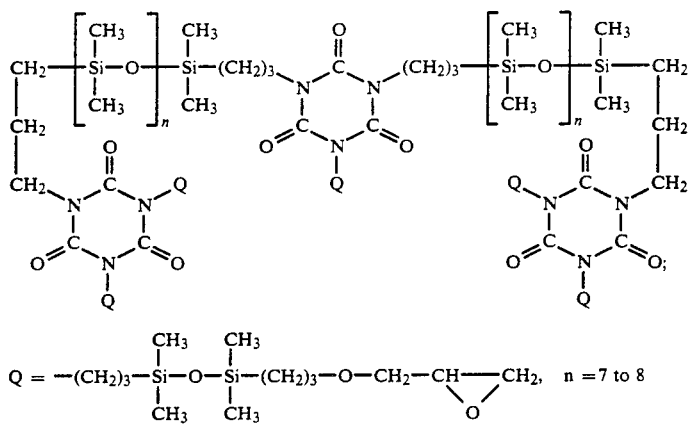

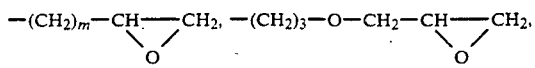

Q = —(CH$_2$)$_3$—Si(CH$_3$)$_2$—O—Si(CH$_3$)$_2$—(CH$_2$)$_3$—O—CH$_2$—CH(O)CH$_2$, n = 7 to 8

In accordance with Example 9, 37.4 g of triallylisocyanurate (0.15 mole) are reacted with 64.5 g of a α, ω-SiH-functional polydimethylsiloxane (0.1 mole) with a SiH content of 0.31 mole/100 g. The reaction product is subsequently reacted with 62.1 g of the organosilicon compound (0.25 mole) prepared according to Example 1, and is then reprocessed. 136 g of the desired product are obtained having the following data:

Viscosity at 25° C.: 800 mPa.s;
Refractive index n$_D^{20}$: 1.4574;
Epoxide value: 0.141 mole/100 g.

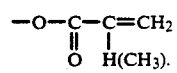

What is claimed is:

1. An isocyanurate-containing, organosilicon compound of the general formula

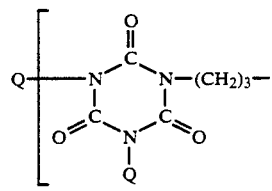

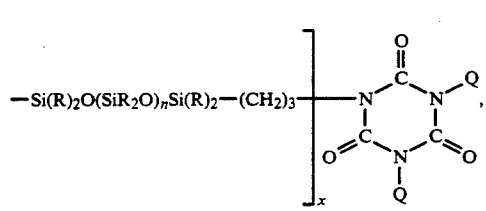

in which Q=—(CH$_2$)$_3$Si(R)$_2$O(SiR$_2$O)$_n$Si(R)$_2$R', n is an integer from 0 to 25 and x is an integer from 0 to 10, and the following holds for the residues R and R', which are the same or different:

R=alkyl, cycloalkyl, aryl, arylalkyl or alkylaryl, and
R'=an epoxy-functional residue with 4 to 10 C-atoms or a (meth)acrylate-functional residue with at least 6 C-atoms.

2. An isocyanurate-containing, organosilicon compound according to claim 1 wherein the epoxy-functional residue has the following structure:

—(CH$_2$)$_m$—CH(O)CH$_2$, —(CH$_2$)$_3$—O—CH$_2$—CH(O)CH$_2$,

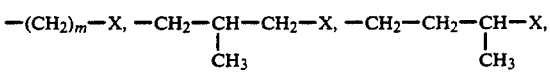

where the following holds: m=2 to 6.

3. An isocyanurate-containing, organosilicon compound according to claim 1 wherein the (meth)acrylate-functional residue has the following structure:

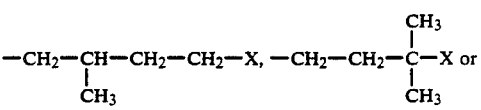

whereby the following holds: m=3 or 4 and X=